(12) United States Patent
Pollack et al.

(10) Patent No.: US 7,638,278 B2
(45) Date of Patent: Dec. 29, 2009

(54) MARKERS OF DNA COPY NUMBER ALTERATION FOR IMPROVED PROGNOSTICATION IN PROSTATE CANCER

(75) Inventors: Jonathan Robert Pollack, Burlingame, CA (US); Jacques Lapointe, Montréal (CA); James Duane Brooks, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 293 days.

(21) Appl. No.: 11/433,844

(22) Filed: May 12, 2006

(65) Prior Publication Data
US 2006/0263814 A1 Nov. 23, 2006

Related U.S. Application Data

(60) Provisional application No. 60/681,073, filed on May 13, 2005.

(51) Int. Cl.
*C07H 21/04* (2006.01)
*C12Q 1/68* (2006.01)

(52) U.S. Cl. .................. 435/6; 435/91.1; 435/91.2; 435/287.2; 536/23.1; 536/24.3

(58) Field of Classification Search .............. None
See application file for complete search history.

(56) References Cited

U.S. PATENT DOCUMENTS 5,427,910 A 6/1995 Kamentsky et al.
5,750,340 A 5/1998 Kim et al.
5,756,696 A 5/1998 Gray et al.

OTHER PUBLICATIONS

Lapointe et al. (Cancer Research, vol. 67, pp. 8504-8510, 2007).*
Petrovics et al. (Oncogene, vol. 24, pp. 3847-3852, 2005).*
Sementchenko et al. (Oncogene, vol. 17, pp. 2883-2888, 1998).*
Amiel et al. (Cancer, vol. 83, pp. 1966-1971, 1998).*
Various Authors, "Initial sequencing and analysis of the human genome," (2001) *Nature*, 409:860-921.
Various Authors, "Finishing the euchromatic sequence of the human genome," (2004) *Nature*, 431:931-945.
Deloukas, P., et al., "The DNA sequence and comparative analysis of human chromosome 10," (2004) *Nature* 429:375-381.
Hattori, M., et al., "The DNA sequence of human chromosome 21," (2000) *Nature*, 405:311-319.
LaPointe, J., et al., "Gene expression profiling identifies clinically relevant subtypes of prostate cancer," (2004) *PNAS*, 101(3):811-816.
Mungall, A.J., et al., "The DNA sequence and analysis of human chromosome 6," (2003) *Nature*, 425:805-812.

(Continued)

*Primary Examiner*—Jeanine A Goldberg
(74) *Attorney, Agent, or Firm*—Bozicevic Field & Francis LLP; Pamela J. Sherwood

(57) ABSTRACT

The invention describes DNA copy number alterations (CNAs), identifiable by technologies such as array-based comparative genomic hybridization (array CGH) or fluorescence in situ hybridization (FISH), that define distinct genetic subtypes of prostate cancer, and are useful for improved prognostication and treatment stratification for patients with prostate cancer.

7 Claims, 2 Drawing Sheets

OTHER PUBLICATIONS

Nusbaum, C., et al., "DNA sequence and analysis of human chromosome 8," (2006) *Nature*, 439:331-335.

Schmutz, J., et al., "The DNA sequence and comparative analysis of human chromosome 5," (2004) *Nature*, 431:268-274.

Venter, J.C., et al., "The sequence of the human genome," (2001) *Science*, 291:1304-1351.

Zody, M., et al., "DNA sequence of human chromosome 17 and analysis of rearrangement in the human lineage," (2006) *Nature*, 440:1045-1049.

* cited by examiner

MARKERS OF DNA COPY NUMBER ALTERATION FOR IMPROVED PROGNOSTICATION IN PROSTATE CANCER

This invention was made with Government support under contracts CA097139 and CA085129 awarded by the National Institutes of Health. The Government has certain rights in this invention.

BACKGROUND OF THE INVENTION

Chromosome abnormalities are often associated with genetic disorders, degenerative diseases, and cancer. The deletion or multiplication of copies of whole chromosomes and the deletion or amplifications of chromosomal segments or specific regions are common occurrences in cancer. In fact, amplifications and deletions of DNA sequences can be the cause of a cancer. For example, proto-oncogenes and tumor-suppressor genes, respectively, are frequently characteristic of tumorigenesis. The identification and cloning of specific genomic regions associated with cancer is therefore of interest both to the study of tumorigenesis and in developing better means of diagnosis and prognosis.

Cancer, like many diseases, is not the result of a single, well-defined cause, but rather can be viewed as several diseases, each caused by different aberrations in informational pathways, which ultimately result in apparently similar pathologic phenotypes. Identification of polynucleotides that correspond to copy number alterations in cancerous, precancerous, or low metastatic potential cells relative to normal cells of the same tissue type, provides the basis for diagnostic tools, facilitates drug discovery by providing for targets for candidate agents, and further serves to identify therapeutic targets for cancer therapies that are more tailored for the type of cancer to be treated.

Identification of differentially altered genomic sequences also furthers the understanding of the progression and nature of complex diseases such as cancer, and is key to identifying the genetic factors that are responsible for the phenotypes associated with development of, for example, the metastatic phenotype. Identification of copy number alterations in various types of cancers can both provide for early diagnostic tests, and further serve as therapeutic targets.

Early disease diagnosis is of central importance to halting disease progression, and reducing morbidity. Analysis of a patient's tumor provides the basis for more specific, rational cancer therapy that may result in diminished adverse side effects relative to conventional therapies. Furthermore, confirmation that a tumor poses less risk to the patient (e.g., that the tumor is benign) can avoid unnecessary therapies.

Adenocarcinoma of the prostate is the most common malignancy in men over 50 yr in the USA; and the incidence increases with each decade of life. Prostate cancer generally is slowly progressive and may cause no initial symptoms, although there is considerable variation in phenotype. In late disease, symptoms of bladder outlet obstruction, ureteral obstruction, and hematuria may appear. Metastases to the pelvis, ribs, and vertebral bodies may cause bone pain. Locally advanced prostate cancer may exhibit extension of induration to the seminal vesicles and fixation of the gland laterally.

There are several known risk factors for getting prostate cancer, including age, ethnicity, genetics and diet. Age is generally considered the most important risk factor for prostate cancer. The incidence of prostate cancer rises quickly after the age of 60, and the majority of men will have some form of prostate cancer after the age of 80. The most common dietary culprit implicated in raising prostate cancer risk is a high fat diet, particularly a diet high in animal fats. Also, a few studies have suggested that a diet low in vegetables causes an increased risk of prostate cancer. A variety of different genetic factors are currently being researched. Men who carry mutations in BRCA1 or BRCA2 genes may have a 2 to 5 fold increase in prostate cancer risk. Men with high levels of testosterone or IGF-1 (insulin-like growth factor 1) also seem to be at a higher risk for developing prostate cancer.

Conventional screening for prostate cancer utilizes the prostate specific antigen (PSA) blood test, and the digital rectal exam (DRE). PSA is an enzyme produced in the prostate that is found in the seminal fluid and the bloodstream. An elevated PSA level in the bloodstream does not necessarily indicate prostate cancer, since PSA can also be raised by infection or other prostate conditions such as benign prostatic hyperplasia (BPH). Many men with an elevated PSA do not have prostate cancer. Nonetheless, a PSA level greater than 4.0 nanograms per milliliter of serum was established initially as the cutoff where the sensitivity for detecting prostate cancer was the highest and the specificity for detecting non-cancerous conditions was the lowest. A PSA level above 4.0 ng per milliliter of serum may trigger a prostate biopsy to search for cancer. The digital rectal exam is usually performed along with the PSA test, to check for physical abnormalities that can result from tumor growth.

The PSA test is an imperfect screening tool. A man can have prostate cancer and still have a PSA level in the "normal" range. Approximately 25% of men who are diagnosed with prostate cancer have a PSA level below 4.0. In addition, only 25% of men with a PSA level of 4-10 are found to have prostate cancer. With a PSA level exceeding 10, this rate jumps to approximately 65%.

With prostate cancer, once a cancer is diagnosed, a key clinical question is whether it will progress to clinically-evident disease and therefore merit treatment. For predicting clinical behavior, i.e. prognostication, the currently used indicators are tumor stage (a measure of tumor spread), tumor grade (a measure of tumor differentiation), and PSA (an indicator of tumor size). These current methods of prognostication are inadequate, because most prostate tumors present with low PSA, intermediate grade and early stage. Markers that would allow the stratification of tumors into genetic subtypes with distinct clinical behaviors are of great interest. Stable markers, such as DNA, are of particular interest. The present invention addresses these needs.

SUMMARY OF THE INVENTION

The present invention relates to the identification and genomic mapping of regions of nucleic acid associated with cancer and tumorigenesis. Methods are provided for determining the presence of a copy number alteration (CNA) in a human sample, where the CNA is associated with prognosis for prostate cancer. A copy number alteration is a variation in the number of copies of a gene or genetic region that are present in the genome of a cell. A normal diploid cell will typically have two copies of each chromosome and the genes contained therein. Copy number alterations may increase the number of copies, or decrease the number of copies.

Probes useful in these methods hybridize to a human genomic nucleic acid sequence comprising one of: the 6q14-q16 region, the 2q21-q24 region, or the 5q21 region; the loss of which are significantly associated with the clinically indolent subtype I tumors, as described herein. Alternatively, probes of interest hybridize to a human genomic nucleic acid sequence comprising one of: the 8p21-p23 region, the 10q23 region, the 17q21 region and the 21q22 region; the loss of which are associated with the clinically-aggressive subtype II tumors, as described herein. In methods of the invention, a human genomic DNA is contacted with one or more of such probes under conditions in which the probe binds selectively to the targeted sequence, and the complex thus formed is detected. The loss of a genomic region in a genomic DNA sample is detected by decreased hybridization of the probe. In one embodiment, the DNA is isolated from a cell suspected of being a prostate tumor cell. Methods of analysis include fluorescence in situ hybridization (FISH) and array based comparative genomic screening.

In the methods of the invention, the probe can also comprise a nucleic acid that hybridizes specifically to a nucleic acid sequence spanning the distance between 6q14 and 6q16, between 2q21 and q24; the 5q21 region; the distance between 8p21 and 8p23; the 10q23 region, the 17q21 region or the 21q22 region; or within any of these regions. Alternatively, a probe may comprise a polymerase chain reaction primer pair capable of amplifying some or all of the nucleic acid sequence from 6q14 to 6q16; from 2q21 to q24; the 5q21 region; from 8p21 to 8p23; the 10q23 region, the 17q21 region; or the 21q22 region. The detection step can comprise detecting the formation of the polymerase chain reaction amplification reaction.

The probe or probes may be attached to a solid surface, for example in an array format. The human nucleic acid may be labeled with a detectable marker, particularly a fluorescently labeled marker. The method may further provide nucleic acids from a reference cell, for example a normal tissue sample, a prostate cancer sample of known stage and diagnosis, and the like.

The invention also provides a kit for screening for the presence of a copy number alteration in a sample of human nucleic acid, the kit comprising a compartment which contains a probe, wherein the probe comprises nucleic acid that hybridizes specifically to a nucleic acid sequence spanning the distance between 6q14 and 6q16, between 2q21 and q24; the 5q21 region; the distance between 8p21 and 8p23; the 10q23 region, the 17q21 region or the 21q22 region; or within any of these regions. The probe or probes can be attached to a solid surface, and may be a member of a nucleic acid array. In another embodiment, the kit comprises one or more polymerase chain reaction primer pair(s) capable of amplifying some or all of the nucleic acid sequence from 6q14 to 6q16; from 2q21 to q24; the 5q21 region; from 8p21 to 8p23; the 10q23 region, the 17q21 region; or the 21q22 region. The kit can further comprise instructional material that indicates that the detection of a loss of the sequence is diagnostic or prognostic of prostate cancer or tumorigenesis.

DETAILED DESCRIPTION OF THE EMBODIMENTS

Figure 1:
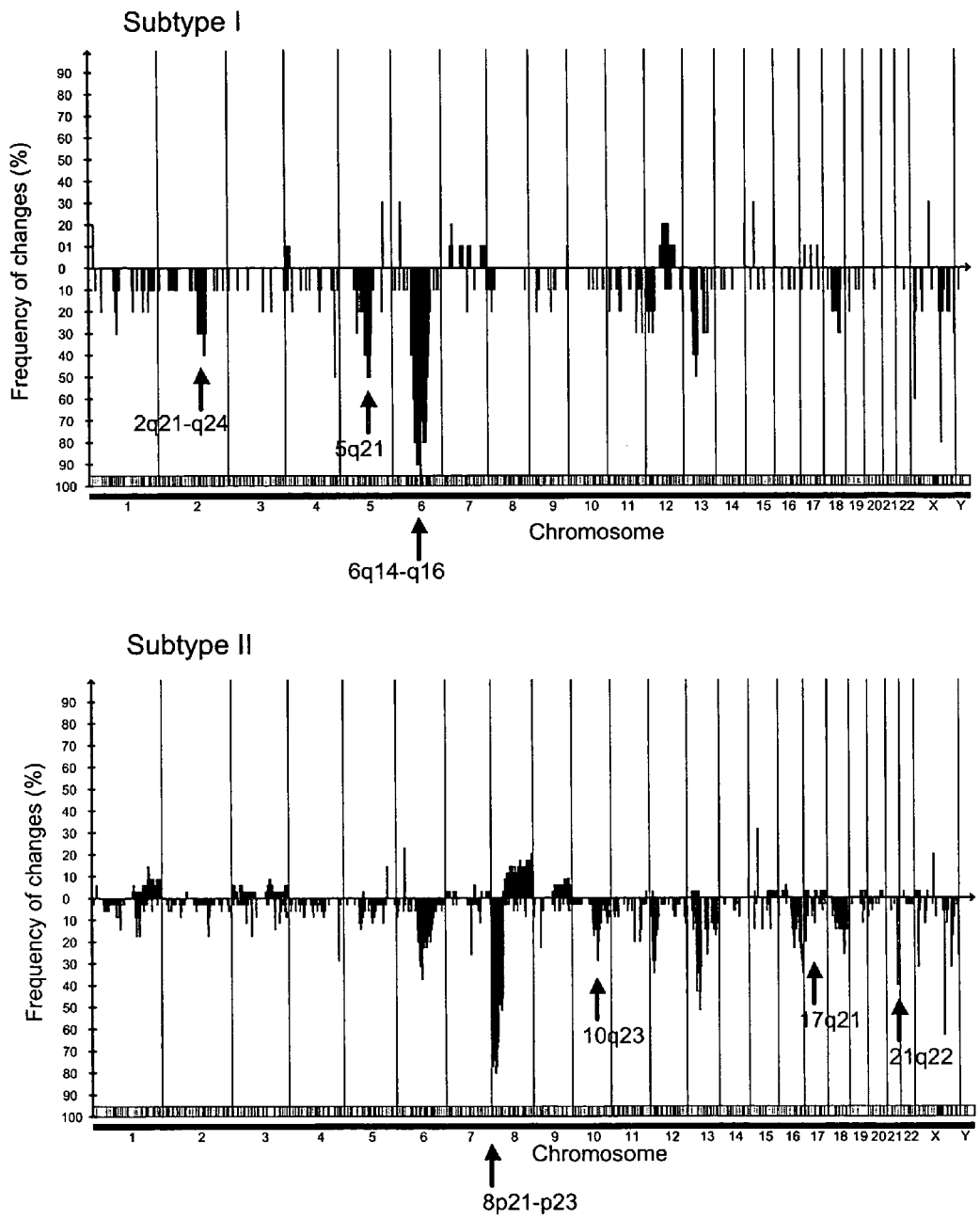
FIG. 1. Consensus plots of CNAs detected by array CGH, for prostate cancer subtype I (top) and subtype II (bottom) tumors. Frequency of CNAs among tumors is plotted against chromosome map position. Note that loss of 2q21-q24, 5q21 and 6q14-q16 are highly significantly associated with clinically indolent subtype I tumors, while loss of 8p21-p23, 10q23, 17q21 and 21q22 are associated with clinically-aggressive subtype II tumors (P<0.01).

The invention identifies human genomic sequences within the regions: 2q21-q24; 5q21; 6q14-16; 8p21-p23; 10q23; 17q21; and 21q22, which are useful for detecting, diagnosing and prognosing human prostate cancer. The nucleic acid regions are associated with chromosomal abnormalities and copy number changes in human prostate cancer. These sequences are used as probes and in methods to detect copy number changes to screen for the presence of disease, and in the prognosis for aggressive tumor behavior and response to therapy.

The invention provides nucleic acid probes for screening for the presence of a copy number alteration in a sample of human genomic nucleic acid. In various embodiments, the probe comprises a nucleic acid that hybridizes specifically to a target genomic sequence in the 2q21-q24; 5q21; 6q14-16; 8p21-p23; 10q23; 17q21; or 21q22 regions. In alternative embodiments, the probe comprises nucleic acid that hybridizes specifically to any nucleic acid sequence spanning the distance between 6q14 and 6q16, between 2q21 and q24; the 5q21 region; the distance between 8p21 and 8p23; the 10q23 region, the 17q21 region or the 21q22 region; or within any of these regions; to any clone, GDB locus or STS marker in the 2q21-q24; 5q21; 6q14-16; 8p21-p23; 10q23; 17q21; or 21q22 regions. Also included are PCR primers that amplify at least a portion of any one of these regions.

Hybridization using the genetic sequences of the invention can also detect copy number changes in the 2q21-q24; 5q21; 6q14-16; 8p21-p23; 10q23; 17q21; or 21q22 regions, which are indicative of the presence of and/or prognosis of cancer, including prostate cancer. The methods comprise contacting the human genomic sequences with a probe under stringent hybridization conditions, detecting the formation of hybridization complexes, and quantifying the target copy number in the sample. Hybridization techniques can also be utilized to identify, isolate and characterize genes and gene products within the target region, including isoforms, alleles and polymorphisms.

Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

DEFINITIONS

The target region as used herein refers to a region of genomic nucleic acid which, when present in altered copy number, is associated with cancer. For example, the invention provides nucleic acid sequences on human chromosome 2q21-q24; 5q21; 6q14-16; 8p21-p23; 10q23; 17q21; or 21q22 regions that are associated with a specific tumor phenotype when absent. Thus, the invention provides a nucleic acid that is used as a probe to analyze changes in copy number to screen and diagnose cancer.

Using high resolution array comparative genomic hybridization ("array CGH") or FISH, sequences from the target region of the invention can be used as a probe to determine single copy number changes in nucleic acid samples. Determination (quantification) of copy number aids in the diagnosis and prognosis of prostate cancer, as loss of copy number is associated with, respectively, clinically indolent subtype I tumors or clinically-aggressive subtype II tumors. In particular, the probes of the invention comprise nucleic acid that hybridizes specifically to the human genomic sequence, in the 2q21-q24; 5q21; 6q14-16; 8p21-p23; 10q23; 17q21; or 21q22 regions. In alternative embodiments, the probe comprises nucleic acid that hybridizes specifically to any nucleic acid sequence spanning the distance between 6q14 to 6q16 or 8p21 to 8p23; to any clone, GDB locus or STS marker in the 2q21-q24; 5q21; 6q14-16; 8p21-p23; 10q23; 17q21; or 21q22 regions.

The sequences of the human genome are known and publicly available, for example through Genbank; and as published by International Human Genome Sequencing Consortium (2004) Nature 431:931-945; International Human Genome Sequencing Consortium (2001) Nature 409:860-921; Venter et al. (2001) Science 291:1304-1351; and in the analysis of individual chromosomes: Zody et al. (2006) Nature 440(7087):1045-9, "DNA sequence of human chromosome 17 and analysis of rearrangement in the human lineage"; Schmutz (2004) Nature 431:268-274, "The DNA sequence and comparative analysis of human chromosome 5"; Mungall et al. (2003) Nature 425, 805-811, "The DNA sequence and analysis of human chromosome 6"; Hattori et al. Nature 405, 311-319 (2000), "The DNA sequence of human chromosome 21"; Deloukas et al. (2004) Nature 429, 375-381, "The DNA sequence and comparative analysis of human chromosome 10"; Nusbaum et al. (2006) Nature 439: 331-335, "DNA sequence and analysis of human chromosome 8".

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. Generally, highly stringent hybridization and wash conditions are selected to be about 5° C. lower than the thermal melting point for the specific sequence at a defined ionic strength and pH.

An example of stringent hybridization conditions for hybridization of complementary nucleic acids that have more than 100 complementary residues on an array or on a filter in a Southern or northern blot is 42° C. using standard hybridization solutions (see, e.g., Sambrook (1989) Molecular Cloning: A Laboratory Manual (2nd ed.) Vol. 1-3, Cold Spring Harbor Laboratory, Cold Spring Harbor Press, N.Y. ("Sambrook") for a description of SSC buffer) with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of more than about 100 nucleotides, is 1×SSC at 45° C. for 15 minutes. An example of a low stringency wash for a duplex of more than about 100 nucleotides, is 4× to 6×SSC at 40° C. for 15 minutes.

Probe Label. The nucleic acid probe is labeled by any convenient technique, e.g. random priming, PCR amplification, etc. The label may be conjugated to a primer, or a component in the pool of nucleotides used in the reaction is labeled, so as to incorporate the label into the product. The use of directly labeled probes in FISH is described in U.S. Pat. No. 5,776,688.

Suitable fluorochromes include fluorescein isothiocyanate (FITC), rhodamine and rhodamine derivatives, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4', 7',4,7-hexachlorofluorescein (HEX), 5-carboxyfluorescein (5-FAM) or N,N,N',N'-tetramethyl-6-carboxyrhodamine (TAMRA), etc. Preferred labels for probes of greater than about 20 kb have a strong signal intensity and its low photo bleaching, e.g. sulfonated rhodamine derivatives such as Alexa 488 (Molecular Probes); spectrum green and spectrum red (Vysis).

Labels also include a two stage system, where the DNA is conjugated to biotin, haptens, etc. having a high affinity binding partner, e.g. avidin, specific antibodies, etc., where the binding partner is conjugated to a detectable label. Exemplary is the use of a digitalis steroid as a hapten, e.g. digoxigenin, or the closely related compounds digitoxin, digitoxigenin and digoxin, which serve as labels on the nucleic acid probe. Antibodies specific for the hapten are then added, and a final fluorescent labeled second stage reagent specific for the first stage antibodies are added. The first and second stage antibodies may be polyclonal or monoclonal antibodies of various isotypes, e.g. IgM, IgA, IgG, usually of the IgG class. Antisera are commercially available from a variety of sources, or may be raised in any convenient animal, e.g. mouse, rat, sheep, goat, etc. The antibodies may be used as intact tetramers, or fragments thereof which maintain the specific binding portion of the molecule, e.g. Fab and F(ab')$_2$ fragments.

The term "nucleic acid" as used herein refers to a deoxyribonucleotide or ribonucleotide in either single- or double-stranded form. The term encompasses nucleic acids, i.e., oligonucleotides, containing known analogues of natural nucleotides that have similar or improved binding properties, for the purposes desired, as the reference nucleic acid. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs). PNAs contain non-ionic backbones, such as N-(2-aminoethyl) glycine units. Other synthetic backbones encompasses by the term include methylphosphonate linkages or alternating methylphosphonate and phosphodiester linkages and benzylphosphonate linkages. The term nucleic acid is used interchangeably with gene, DNA, polynucleotide, cDNA, mRNA, oligonucleotide primer, probe and amplification product.

The term a "nucleic acid array" as used herein is a plurality of target elements, each target element comprising one or more nucleic acid molecules (probes) immobilized on a solid surface to which sample nucleic acids are hybridized. The nucleic acids of a target element can contain sequence from specific genes or clones, such as the probes of the invention. Other target elements will contain, for instance, reference sequences. Target elements of various dimensions can be used in the arrays of the invention. Generally, smaller, target elements are preferred. Typically, a target element will be less than about 1 cm in diameter. Generally element sizes are from 1 μm to about 3 mm, preferably between about 5 μm and about 1 mm.

The target elements of the arrays may be arranged on the solid surface at different densities. The target element densities will depend upon a number of factors, such as the nature of the label, the solid support, and the like. One of skill will recognize that each target element may comprise a mixture of probe nucleic acids of different lengths and sequences. Thus, for example, a target element may contain more than one copy of a cloned piece of DNA, and each copy may be broken into fragments of different lengths. The length and complexity of the probe nucleic acid fixed onto the target element is not critical to the invention. One of skill can adjust these factors to provide optimum hybridization and signal production for a given hybridization procedure, and to provide the required resolution among different genes or genomic locations. In various embodiments, probe sequences will have a complexity between about 1 kb and about 1 Mb, between about 10 kb to about 500 kb, between about 200 to about 500 kb, and from about 50 kb to about 150 kb.

The term "probe" or a "nucleic acid probe", as used herein, is defined to be a collection of one or more nucleic acid fragments whose hybridization to a sample can be detected. The probe may be unlabeled or labeled as described above so that its binding to the target or sample can be detected. The probe is produced from a source of nucleic acids from one or more target portions of the genome, e.g., one or more clones, an isolated whole chromosome or chromosome fragment, or a collection of polymerase chain reaction (PCR) amplification products. The probes of the present invention are produced from nucleic acids found in the regions described herein. The probe or genomic nucleic acid sample may be processed in some manner, e.g. by blocking or removal of repetitive nucleic acids or enrichment with unique nucleic acids.

The word "sample" may be used herein to refer not only to detected nucleic acids, but to the detectable nucleic acids in the form in which they are applied to the target, e.g. with the blocking nucleic acids, etc.

The probe may also be provided as isolated nucleic acids immobilized on a solid surface, as in an array. In some embodiments, the probe may be a member of an array of nucleic acids. Techniques capable of producing high density arrays can also be used for this purpose. One of skill will recognize that the precise sequence of the particular probes described herein can be modified to a certain degree to produce probes that are "substantially identical" to the disclosed probes, but retain the ability to specifically bind to the same targets or samples as the probe from which they were derived. Such modifications are specifically covered by reference to the individual probes described herein.

The term "sample of human nucleic acid" as used herein refers to a sample comprising human DNA or RNA in a form suitable for hybridization to probes of the invention. The nucleic acid may be isolated, cloned or amplified; it may be genomic DNA, mRNA, or cDNA from a particular chromosome, or selected sequences within particular target regions disclosed here. The nucleic acid sample may be extracted from particular cells or tissues. The cell or tissue sample from which the nucleic acid sample is prepared is typically taken from a patient suspected of having prostate cancer, usually a sample comprising the suspected neoplastic cells.

Methods of isolating cell and tissue samples are well known to those of skill in the art and include, but are not limited to tissue sections, needle biopsies, and the like. Frequently the sample will be a clinical sample derived from a patient, including sections of tissues such as frozen sections or paraffin sections taken for histological purposes. The sample can also be derived from supernatants or the cells themselves from cell cultures, cells from tissue culture and other media in which it may be desirable to detect chromosomal abnormalities or determine copy number. In some cases, the nucleic acids may be amplified using standard techniques such as PCR, prior to the hybridization. The sample may be isolated nucleic acids immobilized on a solid. The sample may also be prepared such that individual nucleic acids remain substantially intact.

Prostate Cancer. Prostate cancer, a leading cause of cancer death, displays a broad range of clinical behavior from relatively indolent to aggressive metastatic disease. The widespread use of serum prostate-specific antigen (PSA) screening has led to identification of an increasing number of asymptomatic low-stage tumors in younger men. An important clinical question has become whether and how aggressively to treat such patients with localized prostate cancer. The observed clinical heterogeneity of prostate cancer is likely to reflect underlying molecular heterogeneity among tumors, which, although largely invisible under the light microscope, can be captured by genetic profiling (see, for example, Lapointe et al. (2004) PNAS 101(3):811-816, herein specifically incorporated by reference).

Clinically indolent subtype I tumors are the clinically least aggressive subclass. This subgroup may represent more highly differentiated tumors. This subclass is associated with longer recurrence-free survival, independent of tumor grade and stage. Subtype I, although predominantly comprising low-grade tumors, also included higher-grade tumors, we speculate that expression profiling may identify a molecular signature of differentiation not apparent by histology.

Clinically aggressive subtype II tumors represent a clinically aggressive tumor subclass, being associated with metastasis and tumor recurrence. Although this subgroup can be associated with high grade and advanced stage, it is worth noting that many tumors within subgroup II are low grade and early stage, demonstrating that genetic features provide a characterization relevant to tumor progression that is not appreciable by pathological analysis.

Comparative Genomic Hybridization(Cgh) using Nucleic Acid Arrays

Nucleic acid hybridization assays for the detection of target region sequences, for quantifying copy number, for sequencing, and the like, can be performed in an array-based format. Arrays are a multiplicity of different "probe" or "target" nucleic acids (or other compounds) hybridized with a sample nucleic acid. In an array format a large number of different hybridization reactions can be run in parallel. This provides rapid, essentially simultaneous, evaluation of a large number of loci.

The nucleic acid probes are fixed to a solid surface in an array. These probes comprise portions of the target regions of the invention, optionally in combination with probes from other portions of the genome. Probes can be obtained from any convenient source, including MACs, YACs, BACs, PACs, cosmids, plasmids, inter-Alu PCR products of genomic clones, restriction digests of genomic clones, CDNA clones, amplification products, and the like. The arrays can be hybridized with a single population of sample nucleic acid or can be used with two differentially labeled collections, for example a test sample and a reference sample.

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g. nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition, substances that form gels can be used. Such materials include proteins, lipopolysaccharides, silicates, agarose and polyacrylamides. Where the solid surface is porous, various pore sizes may be employed depending upon the nature of the system.

In preparing the surface, a plurality of different materials may be employed, particularly as laminates, to obtain various properties. For example, proteins such as casein or BSA or mixtures of macromolecules can be employed to avoid nonspecific binding, simplify covalent conjugation, enhance signal detection or the like. If the probe is to be covalently bound, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. For example, methods for immobilizing nucleic acids by introduction of various functional groups to the molecules is known. Covalent attachment of the target nucleic acids to glass or synthetic fused silica can be accomplished according to a number of known techniques and commercially available reagents. For instance, materials for preparation of silanized glass with a number of functional groups are commercially available or can be prepared using standard techniques. Quartz cover slips, which have at least 10-fold lower autofluorescence than glass, can also be silanized.

Alternatively, probes can also be immobilized on commercially available coated beads or other surfaces. For instance, biotin end-labeled nucleic acids can be bound to commercially available avidin-coated beads. Streptavidin or anti-digoxigenin antibody can also be attached to silanized glass slides by protein-mediated coupling. Hybridization to nucleic acids attached to beads is accomplished by suspending them in the hybridization mix, and then depositing them on a substrate for analysis after washing, or analyzing by flow cytometry.

Comparative genomic hybridization (CGH) can detect and map DNA sequence copy number variation throughout the entire genome in a single experiment. In one variation of CGH, the genome is provided as a cytogenetic map through the use of metaphase chromosomes. Alternatively hybridization probes are arrays of genomic sequences containing the target region sequences of the invention, optionally also including other genomic probes. Relative copy number can also be measured by hybridization of fluorescently labeled test and reference nucleic acids in both metaphase chromosome-based and array-based CGH.

In metaphase chromosome-based CGH total genomic DNA is isolated from a "test" and a "reference" cell population, labeled with different fluorochromes, and hybridized to normal metaphase chromosomes. Cot-1 DNA is used to suppress hybridization of repetitive sequences. The resulting ratio of the fluorescence intensities of the two fluorochromes at a location on a chromosome is approximately proportional to the ratio of the copy numbers of the corresponding DNA sequences in the test and reference genomes. Thus, CGH provides genome-wide copy number analysis referenced to the cytogenetic map provided by the metaphase chromosomes. However, the use of metaphase chromosome CGH limits the resolution to 10-20 megabases (Mb), prohibits resolution of closely spaced aberrations, and only allows linkage of CGH results to genomic information and resources with cytogenetic accuracy.

In the methods of the invention, a similar hybridization methodology is used with an array of mapped clones containing target region sequence-containing nucleic acid. This permits measurement of copy number with resolution determined by the size of the probes and/or the map spacing between them. Use of overlapping clones from regions of contiguous clone coverage as probes allows mapping with a genomic resolution less than the clone length (as low as 50 Kb). This methodology also quantitatively measures the copy number of the target sequence.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal, for example antibody-antigen or complementary nucleic acid binding. The label may also allow indirect detection of the hybridization complex. For example, where the label is a hapten or antigen, the sample can be detected by using antibodies. In these systems, a signal is generated by attaching fluorescent or radioactive label or enzymatic molecule to the antibodies. The sensitivity of the hybridization assays can be enhanced through use of a target nucleic acid or signal amplification system that multiplies the target nucleic acid or signal being detected. Alternatively, sequences can be generally amplified using nonspecific PCR primers and the amplified target region later probed for a specific sequence indicative of a mutation.

Various other technologies may also be used for determining copy number. In some embodiments, the method involves amplifications of a test locus with unknown copy number and a reference locus with known copy number using real-time PCR. Progress of the PCR reactions is monitored using fluorigenic probes and a real-time fluorescence detection system.

For each reaction, the number of cycles is measured at which a defined threshold fluorescence emission is reached. Using standard curves, the copy number of the test DNA relative to a common standard DNA is determined for each locus. From the ratio of the relative copy numbers, the genomic copy number of the test locus is determined (see Wilke et al. (2000) Hum Mutat 16:431-436).

Fish

Fluorescence in situ hybridization or immunohistochemistry (IHC) may be used to determine copy number. In FISH, an aliquot of candidate cells is taken from a culture, biopsy section, etc. Protocols for FISH are known in the art. Exemplary is U.S. Pat. No. 5,427,910; U.S. Pat. No. 5,750,340; U.S. Pat. No. 5,756,696, herein incorporated by reference. The cells are transferred to slides. They are then fixed, permeabilized and dehydrated. The slides are hybridized with a probe. Hybridization buffers optimized for FISH are readily available, (e.g. LSI hybridization buffer, Vysis). Particularly with probes prepared from long sequences of greater than 20 kb, it is desirable to include unlabeled repetitive DNA sequences, e.g. chromosomal DNA, Cot-1 DNA, etc. to block the hybridization of the probe to repetitive genomic sequences. The hybridization is allowed to proceed for about 12 to 24 hours, and the slides are then washed to remove non-hybridized probe.

For slides hybridized with directly labeled probes signals are visualized directly, e.g. with a fluorescent microscope. Where an indirect staining is used, e.g. a hapten/antibody combination, the slides are further processed with primary and secondary antibody binding steps. Each slide is examined for fluorescent spots on the interphase nuclei. Analysis of the FISH shows one or no regions of hybridization per genome where there is a loss of the target region; and two for a control locus.

Kits

This invention also provides diagnostic kits for the detection of chromosomal abnormalities or alterations in the target regions. In a preferred embodiment, the kits include one or more probes to the target regions of the invention. The kits can additionally include blocking nucleic acid (i.e., Cot-1 DNA) and instructional materials describing when and how to use the kit contents. The kits can also include one or more of the following: various labels or labeling agents to facilitate the detection of the probes, reagents for the hybridization including buffers, a metaphase spread, bovine serum albumin (BSA) and other blocking agents, tRNA, SDS sampling devices including fine needles, swabs, aspirators and the like, positive and negative hybridization controls and so forth.

Experimental

The invention describes DNA copy number alterations (CNAs), identifiable by technologies such as array-based comparative genomic hybridization (array CGH) or fluorescence in situ hybridization (FISH), that define distinct genetic subtypes of prostate cancer, and are useful for improved prognostication and treatment stratification for patients with prostate cancer. Prostate cancer is currently over-diagnosed (with widespread PSA screening) and over-treated, because it is not clear which patients will benefit from treatment; this invention addresses this key clinical problem.

In DNA microarray studies, we identified clinically-relevant subtypes of prostate cancer based on distinct patterns of gene expression (Lapointe et al, 2004, PNAS). Now, using array CGH, we have defined distinct CNAs that underlie these subtypes. Specifically, loss of chromosome region 6q14-16 is associated with relatively indolent tumors, while loss of 8p21-23 is associated with more aggressive tumors. Combining information from both loci is even more informative. These CNA markers can be used for improved patient prognostication, and for improved treatment stratification (e.g. "watchful waiting" vs. aggressive therapy). DNA loss is scoreable by array CGH and FISH, or by other comparable methods.

The results of array CGH are shown in FIG. 1, with consensus plots of CNAs detected by array CGH, for prostate cancer subtype I (top) and subtype II (bottom) tumors. Frequency of CNAs among tumors is plotted against chromosome map position. Loss of 6q14-q16, the 2q21-q24 region, or the 5q21 region is highly significantly associated with the clinically indolent subtype I tumors, while loss of 8p21-p23, the 10q23 region, the 17q21 region and the 21q22 region is associated with the clinically-aggressive subtype II tumors.

Figure 2:
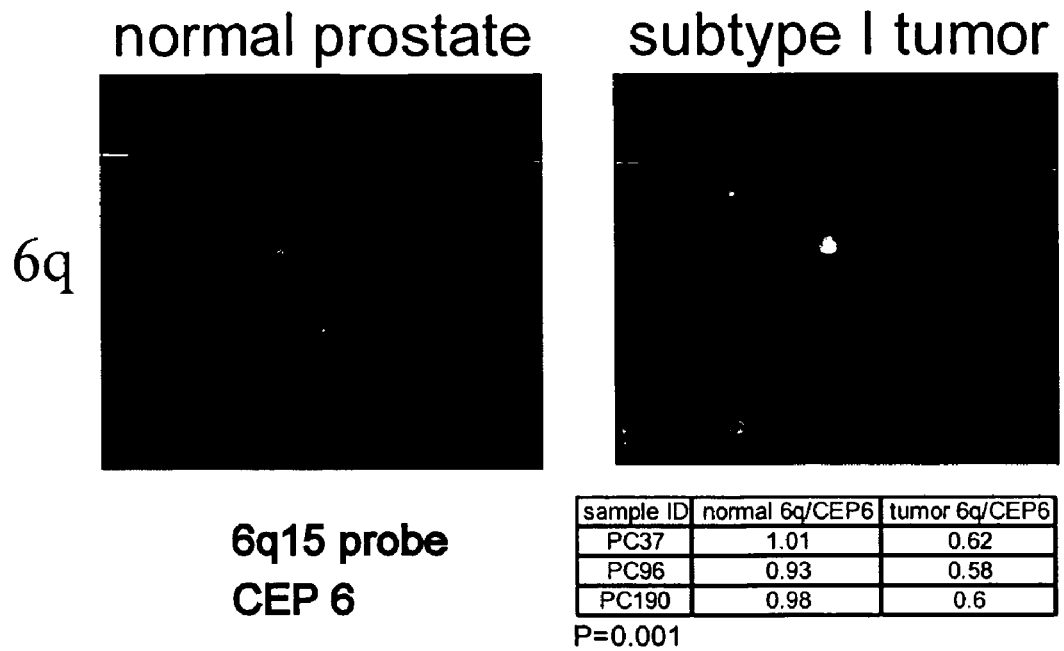
FIG. 2. FISH validation of association between specific CNAs and tumor subtypes. FISH images illustrate deletion of 6q locus in tumor subtype I cases (top panel) and deletion of 8p locus in subtype II cases (bottom panel). Note that only one test locus spot is visible in tumor nuclei (arrow), compared to two centromere spots. In normal prostate cells, two spots each of test and centromere loci are visible. FISH scoring of three tumor and three normal cases demonstrates statistically significant differences in FISH spot counts (indicated).
Figure 2:
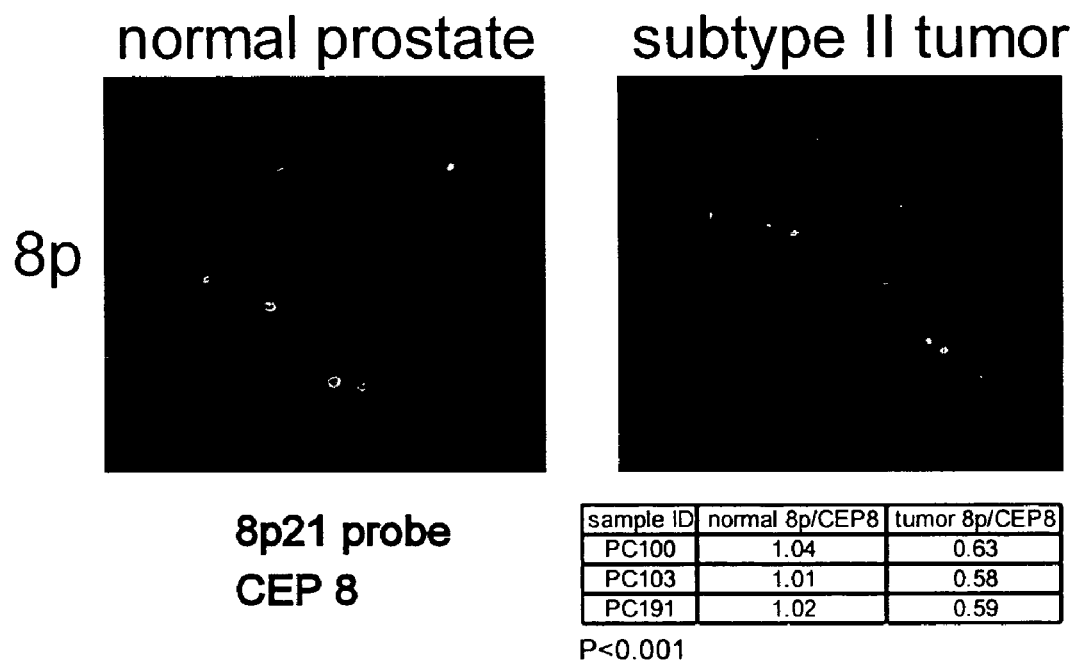

These results were validated by FISH, as shown in FIG. 2. FISH images illustrate deletion of 6q locus in tumor subtype I cases (top panel) and deletion of 8p locus in subtype II cases (bottom panel). Test locus (6q or 8p ) is colored red, and control centromere locus is labeled green. Note that only one red test locus spot is visible in tumor nuclei (red arrow), compared to two green centromere spots. In normal prostate cells, two spots each of test and centromere loci are visible. FISH scoring of three tumor and three normal cases demonstrates statistically significant differences in FISH spot counts.

What is claimed is:

1. A method for phenotyping a cancer sample, the method comprising:
    screening for the presence of a copy number alteration in a sample of human genomic DNA isolated from a suspected primary prostate tumor cell by hybridizing a probe comprising a nucleic acid that hybridizes specifically to a target genomic sequence in the 21q22 region and detecting the formation of the hybridization complex,
    wherein a reduction of hybridization complexes relative to a normal control is indicative of loss of the 21g22 region and is associated with a clinically-aggressive subtype II tumor.

2. The method according to claim 1, wherein said method further comprises hybridizing a probe to said sample comprising a nucleic acid that hybridizes specifically to any nucleic acid sequence spanning the distance between the distance between 8p21 and 8p23; the 10q23 region, the 17q21 region and the 21q22 region.

3. The method according to claim 1, wherein said method further comprises hybridizing a pair of nucleic acid primers that specifically amplify at least a portion of the region between 8p21 and 8p23; the 10q23 region, the 17q21 region and the 21q22 region.

4. The method of claim 1, wherein the probe is attached to a solid surface.

5. The method of claim 4, wherein the attached probe is a member of a nucleic acid array.

6. The method of claim 1, wherein the human genomic DNA is detectably labeled.

7. The method of claim 1, wherein said probe is detectably labeled.

* * * * *